(12) United States Patent
Abe et al.

(10) Patent No.: US 7,700,232 B2
(45) Date of Patent: Apr. 20, 2010

(54) NONAQUEOUS ELECTROLYTIC SOLUTION FOR LITHIUM SECONDARY BATTERY

(75) Inventors: Koji Abe, Yamaguchi (JP); Yoshihiro Ushigoe, Yamaguchi (JP); Akikazu Ito, Yamaguchi (JP)

(73) Assignee: UBE Industries, Ltd., Ube-Shi, Yamaguchi (JP)

( * ) Notice: Subject to any disclaimer, the term of this patent is extended or adjusted under 35 U.S.C. 154(b) by 765 days.

(21) Appl. No.: 10/593,231

(22) PCT Filed: Mar. 18, 2005

(86) PCT No.: PCT/JP2005/005022

§ 371 (c)(1),
(2), (4) Date: Sep. 18, 2006

(87) PCT Pub. No.: WO2005/091423

PCT Pub. Date: Sep. 29, 2005

(65) Prior Publication Data

US 2008/0248399 A1 Oct. 9, 2008

(30) Foreign Application Priority Data

Mar. 19, 2004 (JP) ............................. 2004-079693

(51) Int. Cl.
*H01M 6/04* (2006.01)

(52) U.S. Cl. .................. 429/200; 429/199; 429/326; 429/327; 429/336; 252/62.2

(58) Field of Classification Search ................. 429/326, 429/327, 336, 199, 200; 252/62.2
See application file for complete search history.

(56) References Cited

U.S. PATENT DOCUMENTS

2004/0121239 A1 6/2004 Abe et al.
2005/0053843 A1* 3/2005 Takahashi .................... 429/329

FOREIGN PATENT DOCUMENTS

JP 2004-063367 2/2004
WO WO 02/059999 8/2002

OTHER PUBLICATIONS

International Preliminary Report On Patentability and Written Opinion of the International Searching Authority, PCT/JP2005/005022, Nov. 23, 2006.
International Search Report, PCT/JP2005/005022, Jun. 28, 2005.

* cited by examiner

*Primary Examiner*—Laura S Weiner
(74) *Attorney, Agent, or Firm*—Nixon Peabody LLP; Jeffrey L. Costellia

(57) ABSTRACT

Disclosed is a nonaqueous electrolytic solution useful for producing a lithium secondary battery having excellent cycle characteristics. Specifically disclosed is a nonaqueous electrolytic solution for lithium secondary batteries obtained by dissolving an electrolyte salt in a nonaqueous solvent which is characterized by containing 0.1 to 10 wt. % of a tert-alkylbenzene compound and also containing 0.001-0.5 wt. % of a benzene compound, wherein a hydrocarbon group having 1-4 carbon atoms is bonded to a benzene ring via the tertiary carbon atom, relative to the tert-alkylbenzene compound.

11 Claims, No Drawings

NONAQUEOUS ELECTROLYTIC SOLUTION FOR LITHIUM SECONDARY BATTERY

FIELD OF THE INVENTION

The present invention relates to a non-aqueous electrolytic solution containing a tert-alkylbenzene compound of high purity used in preparation of a lithium secondary battery which is excellent in battery performance. In more detail, gas generation from decomposition in the prepared battery is inhibited while repeatedly employing the battery or storing it at an elevated temperature. The invention also relates to a lithium secondary battery using the solution. The invention further relates to a method for preparation of a tert-alkylbenzene compound of high purity used as an additive for the non-aqueous electrolytic solution for lithium secondary battery.

BACKGROUND OF THE INVENTION

The lithium secondary battery has recently been widely used, for example, as an electric source for driving small-sized electronic devices. The lithium secondary battery comprises a positive electrode, a negative electrode and a non-aqueous electrolytic solution. The positive electrode generally comprises a complex oxide of lithium such as, $LiCoO_2$, and the negative electrode generally comprises a carbonaceous material or metallic lithium. A carbonate such as ethylene carbonate (EC) and propylene carbonate (PC) has favorably been used in the non-aqueous electrolytic solution for the lithium secondary battery.

The lithium secondary battery requires a further improvement on battery performances such as cycle characteristics of the battery and electric capacity as well as safety.

Japanese Patent Provisional Publication No. H10-275632 discloses that a lithium secondary battery improved in safety can be provided by containing an aromatic ester such as trimellitic ester or phthalic ester, or an alkylbenzene compound such as toluene or butylbenzene (including tert-butylbenzene). However, a further improvement is required on cycle performance. Particularly, the cycle performance and storage stability at high temperatures are insufficient in the case that the lithium secondary battery is used at a high voltage charge potential of 4.2 V or more or at a higher energy density. Further, such a problem has been found that a gas is generated to expand the battery under the above-mentioned conditions.

Japanese Patent Provisional Publication No. 2002-298909 and the pamphlet of WO 02/29922 describe that cycle characteristics, electric capacity and storage characteristics of the lithium secondary battery can be improved by adding a compound having a tert-alkyl group having 5 or more carbon atoms such as tert-pentylbenzene as the tert-alkylbenzene compound to an electrolyte solvent of a lithium secondary battery.

A process for preparation of tert-alkylbenzene compound has been known. For example, tert-pentylbenzene has been prepared by (1) a process of reacting benzene with isoamyl halide in the presence of an acid catalyst (disclosed in J. Am. Chem. Soc., 74, 292(1952)), (2) a process of reacting benzene with isoamylene in the presence of an acid catalyst (disclosed in a. Am. Chem. Soc., 78, 2000(1956)), or (3) a process of reacting cumene with ethylene in the presence of an alkali catalyst (disclosed in U.S. Pat. No. 4,179,472).

The present inventors have studied and found that the tert-alkylbenzene compound prepared according to the known processes contains a trace amount of by-products as impurities. The by-product is a benzene compound having a benzene ring substituted with a hydrocarbon group having 1 to 4 carbon atoms via at least one tertiary carbon atom. Meanwhile, it is difficult to obtain an alkyl halide of high purity or an isoalkylene of high purity. The inventors have further found that the impurities are inevitably produced by a side reaction, even if the materials of high purity were reacted. Moreover, the impurities have boiling points near those of the tert-alkylbenzene compounds. If once the produced impurities are mixed with the product, it is industrially difficult to isolate or purify the product. If the reaction product were isolated and purified from the impurities in a conventional manner, the reaction yield would greatly decrease.

DISCLOSURE OF THE INVENTION

Problems to be Solved by the Invention

An object of the present invention is to improve safety of a lithium secondary battery particularly in the case that the battery is used at a high voltage charge potential of 4.2 V or more or at a higher energy density. Another object of the invention is to provide a non-aqueous electrolytic solution advantageously used as a component of an excellent lithium secondary battery, which can show the cycle performance or storage characteristics of a high level even at a high temperature, and is prevented from expansion caused with gas generation.

Invention to Solve the Problem

The present inventors have found a new method for preparing at a high yield a pure tert-alkylbenzene compound containing a decreased amount of the benzene compound having a benzene ring which is substituted with a hydrocarbon group having 1 to 4 carbon atoms via at least one tertiary carbon atom. The new method comprises subjecting a reaction product obtained by alkylation of a benzene compound according to the conventional process to photo-halogenation. A lithium secondary battery improved in the cycle performance is produced by incorporating thus prepared pure tert-alkylbenzene compound into a non-aqueous electrolytic solution.

Therefore, the present invention resides in a non-aqueous electrolytic solution for a lithium secondary battery which comprises an electrolyte salt in a non-aqueous solvent, which contains a tert-alkylbenzene compound in an amount of 0.1 to 10 wt. % based on an amount of the solution and which further contains a benzene compound having a benzene ring substituted with a hydrocarbon group having 1 to 4 carbon atoms via at least one tertiary carbon atom, in an amount of 0.00001 to 0.05 wt. % based on the amount of the solution.

The invention further resides in a lithium secondary battery comprising a positive electrode, a negative electrode and a non-aqueous electrolytic solution comprising an electrolyte salt in a non-aqueous solvent, wherein the non-aqueous electrolytic solution is the non-aqueous electrolytic solution of the invention described above.

The invention furthermore resides in a method for preparing a pure tert-alkylbenzene compound, which comprises subjecting a reaction product which is obtained by alkylation of a benzene compound and which contains a benzene compound having a benzene ring substituted with a hydrocarbon group having 1 to 4 carbon atoms via at least one tertiary carbon atom to photo-halogenation.

Effect of the Invention

Use of the non-aqueous electrolytic solution of the present invention enables to provide a lithium secondary battery improved in safety. The provided battery is also excellent in cycle performance and storage performance at a high temperature. Further, generation of a gas decreases to prevent the battery from expansion.

BEST MODE FOR THE INVENTION

The reaction product comprising a tert-alkylbenzene compound and a small amount of the impurities can be prepared by an alkylation of a benzene compound in a conventional manner as is described in J. Am. Chem. Soc., 74, 292(1952) or J. Am. Chem. Soc., 78, 2000(1956). This tert-alkylbenzene compound is named "crude tert-alkylbenzene compound".

In the method of the present invention for preparation of a tert-alkylbenzene compound with high purity, the crude tert-alkylbenzene compound obtained in the conventional manner is subjected to a photo-halogenation reaction in the presence of a halogen (e.g., bromine) using a light source. In the reaction procedure, the halogen is selectively added to the tertiary carbon atom attached to the benzene ring of the impurities contained in the tert-alkylbenzene compound such as tert-butylbenzene, tert-pentylbenzene or 1,3-di-tert-butylbenzene. Thus produced compound has a boiling point higher than that of the tert-alkylbenzene compound. The reaction mixture obtained by the reaction procedure is subjected to conventional purification such as precision distillation, to obtain a tert-alkylbenzene compound with a high purity, which contains almost no above-mentioned impurities. The obtained tert-alkylbenzene of high purity is incorporated into a non-aqueous electrolytic solution to prepare a lithium secondary battery improved in cycle performance and storage performance.

The influence of the impurities in the non-aqueous electrolytic solution is considered as described below.

A hydrogen atom on the carbon atom substituent of the benzene compound having a benzene ring substituted with a hydrocarbon group having 1 to 4 carbon atoms via a tertiary carbon atom is more easily abstracted as a radical, as compared with a hydrogen atom on a secondary or primary carbon atom of a benzene compound having a benzene ring substituted with a hydrocarbon group via the secondary or primary carbon atom. Therefore, the former benzene compound shows an oxidation potential lower than that of the tert-alkylbenzene compound. For example, while tert-butyl benzene and tert-pentylbenzene show oxidation potentials of 4.9 V and 4.8 V, respectively, both of isopropylbenzene and sec-butylbenzene show such a lower oxidation potential as 4.6. A part of the alkylbenzene compound having a tertiary carbon atom attached to the phenyl group easily decomposes by oxidation or polymerizes, to cause gas generation and lowering of the cycle performance in the course of the repeated charge-discharge procedure of the battery. Further, thus produced polymer is dissolved to cause lowering safety of the battery.

The photo-halogenation procedure (photo-halogenation reaction) is performed by a light source such as a mercury lamp, a halogen lamp or an UV lamp. The photo-halogenation can be conducted at ordinary, increased or reduced pressure.

Halogen used for the photo-halogenation is fluorine, chlorine, bromine or iodine. Bromine is particularly preferred.

The amount of halogen preferably is in the range of the equivalent mole to five times moles, and more preferably in the range of the equivalent mole to three times moles based on the amount of the impurities contained in the tert-alkylbenzene compound. In the case that the amount is less than the equivalent mole of the impurities, an alkylbenzene compound having a tertiary carbon atom adjacent to the phenyl group might not react and remain. In the case that the amount is more than five times moles, it is necessary to remove an excessive amount of halogen.

As for the halogen used in the photo-halogenation in an appropriate way, bromine or iodine can be dropwise added. Fluorine or chlorine can be diluted with an inert gas. The crude tert-butylbenzene compound can be placed in bromine or iodine. Otherwise, bromine or iodine can be added to the crude tert-butylbenzene compound.

The photo-halogenation procedure is conducted usually at −20° C. to 165° C., preferably at 10° C. to 120° C., and most preferably at 40° C. to 80° C. The procedure can basically be complete in a moment. However, the reaction is usually continued for 1 to 24 hours, and preferably continued for 5 to 12 hours to remove an excessive amount of the above-mentioned halogen compounds such as, halogen or hydrogen halide from the product after the process.

Hydrogen halide generated in the photo-halogenation procedure can be removed by (1) a procedure of bubbling with an inert gas, (2) a procedure of treatment with an inorganic base compound, (3) a procedure of treatment with a metal alkoxide, or (4) a procedure of treatment with a basic organic compound such as, an amine. The examples of the compounds used in the procedures are described below. Examples of the inorganic base compounds include sodium carbonate, sodium hydrogencarbonate, potassium carbonate, sodium hydroxide, potassium hydroxide, magnesium oxide, calcium oxide and barium oxide. Examples of the metal alkoxides include sodium methoxide, sodium ethoxide, sodium n-propoxide, sodium isopropoxide, sodium n-butoxide and sodium tert-butoxide. A metal alkoxide such as an oxide of lithium, potassium, calcium or aluminum can be used in place of sodium oxide. The amine can be a linear or cyclic amine. Examples of the linear amines include triethylamine, tributylamine and diisopropylethylamine. Examples of the cyclic amines include pyridine, pyrrolidine, N-methylpyrrolidine, piperidine, N-methylpiperidine, and 1,8-diazabicyclo[5.4.0]-7-undecene. These compounds can be used in mixture with a solvent such as, water or an alcohol.

The product obtained after the photo-halogenation procedure is preferably subjected to rectification to recover a tert-alkylbenzene compound with high purity. A rectification column having 2 to 100 plates as theoretical plates is preferably used at an ordinary or reduced pressure to conduct the rectification. The reflux ratio preferably is in the range of 2 to 50. Before the photo-halogenation procedure, the crude tert-butylbenzene compound containing impurities is also preferably subjected to distillation for separation and purification procedure of distillation such as, rectification.

In the present invention, impurities to be removed are benzene compounds having a benzene ring substituted with a hydrocarbon group having 1 to 4 carbon atoms via a tertiary carbon atom. Examples of the impurities include isopropylbenzene, sec-butylbenzene, 1,2-dimethylpropylbenzene, 1-tert-butyl-3-isopropylbenzene, 1,2-dimethylindan and 1,3-dimethylindan. Particularly, a linear alkylbenzene compound contained as impurities might degrade the cycle performance. The hydrocarbon group having 1 to 4 carbon atoms of the benzene compound can have a linear or branched structure. An end of the hydrocarbon group opposite to the tertiary carbon atom can be combined to the benzene ring to form a ring. The opposite end of the hydrocarbon group cannot be combined to the tertiary carbon atom.

In the present invention, effective ingredients of the non-aqueous electrolytic solution are tert-alkylbenzene compounds. Examples of the tert-alkylbenzene compounds include tert-butylbenzene, tert-pentylbenzene, 1,3-di-tert-butylbenzene, 1,4-di-tert-butylbenzene, 4-fluoro-tert-butylbenzene, 4-tert-butylbiphenyl, 1,3-di-tert-pentylbenzene, 1,4-di-tert-pentylbenzene and 1-tert-butyl-4-tert-pentylbenzene. The effective ingredient preferably is selected from the group consisting of tert-butylbenzene, tert-pentylbenzene and 1,3-di-tert-butylbenzene.

Combinations of the impurities (benzene compound having a benzene ring substituted with a hydrocarbon group having 1 to 4 carbon atoms via a tertiary carbon atom) with the effective ingredients (the tert-alkylbenzene compounds) in the present invention can be shown below:

(1) A combination of sec-butylbenzene or isopropyl-benzene with tert-butylbenzene;

(2) A combination of isopropylbenzene, 1,2-dimethylpropylbenzene, 1,2-dimethylindan, 1,3-dimethylindan or 1-methyltetrahydronaphthalene with tert-pentylbenzene;

(3) A combination of 1-tert-butyl-3-isopropylbenzene with 1,3-di-tert-butylbenzene;

(4) A combination of 1-tert-butyl-4-isopropylbenzene with 1,4-di-tert-butylbenzene;

(5) A combination of 4-fluoro-isopropylbenzene or 4-fluoro-sec-butylbenzene with 4-fluoro-tert-butylbenzene;

(6) A combination of 4-sec-butylbiphenyl with 4-tert-butylbiphenyl;

(7) A combination of 1-tert-pentyl-3-isopropylbenzene with 1,3-di-tert-pentylbenzene;

(8) A combination of 1-tert-pentyl-4-isopropylbenzene with 1,4-di-tert-pentylbenzene; and (9) A combination of 1-tert-butyl-4-isopropylbenzene with 1-tert-butyl-4-tert-pentylbenzene.

The amount of the impurities (namely, the benzene compound having a benzene ring substituted with a hydrocarbon group having 1 to 4 carbon atoms via a tertiary carbon atom) contained in the non-aqueous electrolytic solution of the invention preferably is 0.5 wt. % or less, more preferably 0.3 wt. % or less, and most preferably 0.1 wt. % or less, based on the amount of the tert-alkylbenzene compound. On the other hand, there is no specific need of reducing the amount of the impurities to 0.001 wt % or less based on the amount of the tert-alkylbenzene compound. The amount of the tert-alkylbenzene compound preferably is in the range of 0.1 to 10 wt. %, more preferably in the range of 0.5 to 5 wt. %, and most preferably in the range of 1 to 3 wt. %, based on the amount of the non-aqueous electrolytic solution.

The non-aqueous electrolytic solution contains a non-aqueous solvent such as a cyclic carbonate compound and a linear carbonate compound.

The cyclic carbonate compound preferably comprises at least one compound selected from the group consisting of ethylene carbonate, propylene carbonate, butylene carbonate, vinylene carbonate, dimethylvinylene carbonate, vinylethylene carbonate and fluoroethylene carbonate. The cyclic carbonate compound more preferably comprises at least two compounds selected from the group consisting of ethylene carbonate, propylene carbonate, vinylene carbonate, vinylethylene carbonate and fluoroethylene carbonate. The cyclic carbonate compound most preferably comprises ethylene carbonate, vinylene carbonate or fluoroethylene carbonate.

Examples of the linear carbonate compounds include linear carbonate compounds having an alkyl group such as dimethyl carbonate (DMC), methyl ethyl carbonate (MEC), diethyl carbonate (DEC), methyl propyl carbonate (MPC), dipropyl carbonate (DPC), methyl butyl carbonate (MBC) and dibutyl carbonate (DBC). The alkyl group can have a straight or branched chain structure.

The proportion of the cyclic carbonate compound and the linear carbonate compound in the non-aqueous solvent preferably is in the range of 20:80 to 40:60 in terms of a volume ratio, and more preferably in the range of 20:80 to 35:65.

The linear carbonate compound preferably has a methyl group to reduce the viscosity. Accordingly, the linear carbonate compound preferably is dimethyl carbonate or methyl ethyl carbonate. Methyl ethyl carbonate, which has a low viscosity, a melting point of not higher than −20° C. and a boiling point of not lower than 100° C., is a particularly preferred asymmetrical linear carbonate compound. The asymmetrical linear carbonate compound, namely methyl ethyl carbonate can be used in combination with a symmetrical linear carbonate compound, such as dimethyl carbonate and diethyl carbonate in a volume ratio of 100:0 to 51:49 (particularly, 100:0 to 70:30).

Examples of electrolyte salts used in the invention include: $LiPF_6$, $LiBF_4$, $LiClO_4$; lithium salts comprising a chain alkyl group such as, $LiN(SO_2CF_3)_2$, $LiN(SO_2C_2F_5)_2$, $LiC(SO_2CF_3)_3$, $LiPF_4(CF_3)_2$, $LiPF_3(C_2F_5)_3$, $LiPF_3(CF_3)_3$, $LiPF_3(iso-C_3F_7)_3$, and $LiPF_5(iso-C_3F_7)$; and lithium salts comprising a cyclic alkylene group such as, $(CF_2)_2(SO_2)_2NLi$, and $(CF_2)_3(SO_2)_2NLi$. More preferred are $LiPF_6$, $LiBF_4$ and $LiN(SO_2CF_3)_2$, and most preferred is $LiPF_6$. The electrolyte salt can be used singly or in combination.

Examples of the preferred combinations include a combination of $LiPF_6$ with $LiBF_4$, a combination of $LiPF_6$ with $LiN(SO_2CF_3)_2$, and a combination of $LiBF_4$ with $LiN(SO_2CF_3)_2$. Most preferred is the combination of $LiPF_6$ with $LiBF_4$. There is no specific limitation with respect to the mixing ratio of the two or more electrolyte salts. In the case that $LiPF_6$ is mixed with other electrolyte salts, the amount of the other electrolyte salts preferably is 0.01 mole % or more, more preferably 0.05 mole % or more, and most preferably 0.1 mole % or more, based on the total amount of the electrolyte salts. The amount of the other electrolyte salts also preferably is 45 mole % or less based on the total amount of the electrolyte salts, more preferably 20 mole % or less, further preferably 10 mole % or less, and most preferably 5 mole % or less. The concentration of the electrolyte salts in the non-aqueous solvent preferably is 0.3 M or more, more preferably 0.5 M or more, further preferably 0.7 M or more, and most preferably 0.8 M or more. Further, the concentration preferably is 2.5 M or less, more preferably 2.0 M or less, further preferably 1.6 M or less, and most preferably 1.2 M or less.

The electrolytic solution of the invention can be obtained, for example by preparing a non-aqueous solvent containing a cyclic carbonate compound and a linear carbonate compound, and then dissolving an electrolyte salt and the tert-alkylbenzene compound of high purity obtained by removing the impurities (namely, the benzene compound having a benzene ring substituted with a hydrocarbon group having 1 to 4 carbon atoms via a tertiary carbon atom) in the solvent.

The non-aqueous electrolytic solution of the invention can contain air or carbon dioxide to reduce gas generation caused by decomposition of the electrolytic solution and to improve battery performances such as, cycle and storage performances.

Carbon dioxide or air can be incorporated (dissolved) into the non-aqueous electrolytic solution according to a method (1) of bringing the non-aqueous electrolytic solution into contact with air or a carbon dioxide-containing gas to introduce the air or gas into the solution, and then injecting the solution into a battery, or a method of (2) injecting the non-aqueous electrolytic solution into the battery, and then introducing air or a carbon dioxide-containing gas into the battery before or after sealing the battery. The two methods can be used in combination. The amount of the moisture contained in the air or carbon dioxide-containing gas preferably is as small as possible. The amount of the moisture is so reduced that the due point of the air or gas preferably is lower than −40° C., and more preferably lower than −50° C.

The non-aqueous electrolytic solution of the present invention is used for manufacturing a lithium secondary battery. There is no specific limitation with respect to materials of the lithium secondary battery other than the non-aqueous electrolytic solution of the invention. The materials employed for the conventional lithium secondary battery can be used in the lithium secondary battery of the invention.

The positive electrode active material preferably is a complex oxide of lithium with cobalt, manganese or nickel. The positive electrode active material can be used singly or in combination. Examples of the complex lithium oxides include $LiCoO_2$, $LiMn_2O_4$, $LiNiO_2$, $LiCo_{1-x}Ni_xO_2$ (0.01<x<1), $LiCo_{1/3}Ni_{1/3}Mn_{1/3}O_2$ and $LiNi_{0.5}Mn_{1.5}O_4$. The two or more positive electrode active materials can be used in mixture in an appropriate way. Examples of the mixtures include a mixture of $LiCoO_2$ with $LiMn_2O_4$, a mixture of $LiCoO_2$ with $LiNiO_2$, and a mixture of $LiMn_2O_4$ with $LiNiO_2$. The material more preferably is a complex lithium oxide that can be used at a voltage of 4.3 V or more when the voltage of an open-circuit is measured using lithium as reference after completing the charge. Examples of the complex lithium oxides that can be used at a voltage of 4.3 V or more include $LiCoO_2$, $LiMn_2O_4$ and $LiNiO_2$. The material further preferably is a complex lithium oxide that can be used at a voltage of 4.4 V or more such as $LiCo_{1/3}Ni_{1/3}Mn_{1/3}O_2$ and $LiNi_{0.5}Mn_{1.5}O_4$. The positive electrode active material most preferably is a complex metal oxide of lithium containing Co or Ni. A portion of a complex metal oxide of lithium can be replaced with another metal. For example, a portion of Co contained in $LiCoO_2$ can be replaced with Sn, Mg, Fe, Ti, Al, Zr, Cr, V, Ga, Zn or Cu.

A chemically inert electroconductive material can be used as a conductive material for the positive electrode. Examples of the conductive materials include graphites such as, natural graphite (e.g., scaly graphite), artificial graphite, and carbon blacks such as, acetylene black, kitchen black, channel black, furnace black, lamp black, and thermal black. Graphite and carbon black can be used in combination at an optional mixing ratio. The positive electrode composite contains the conductive material preferably in an amount of 1 to 10 wt. %, and more preferably in an amount of 2 to 5 wt. %.

The positive electrode can be formed by mixing a positive electrode active material with the conductive material such as, acetylene black or carbon black, and a binder to prepare a positive electrode composition, coating a collecting sheet with a positive electrode material, and heating them at a temperature of about 50° C. to 250° C. for about 2 hours under reduced pressure. Examples of the binders include polytetrafluoroethylene (PTFE), polyvinylidene fluoride (PVDF), styrene/butadiene copolymer (SBR), acrylonitrile/butadiene copolymer (NBR), and carboxymethylcellulose (CMC). Examples of the collecting materials include aluminum foil and a stainless lath board.

A material capable of absorbing and releasing lithium can be used as the negative electrode (negative electrode active material). Examples of the materials include: metallic lithium or lithium alloy; a carbonaceous material such as, thermally decomposed carbon, coke, graphite (e.g., artificial graphite, natural graphite), a combustion product of an organic polymeric compound, or carbon fiber; tin or a tin compound; and silicon or a silicon compound. The carbonaceous material preferably has a distance ($d_{002}$) between lattice faces (002) of 0.340 nm or less. The carbonaceous material more preferably is graphite having a graphitic crystal structure with the distance ($d_{002}$) in the range of 0.335 to 0.340 nm.

The negative electrode active material can be used singly or in combination. A powdery material such as, a powder of carbonaceous material can be used as a negative electrode composition by mixing with a binder. Examples of the binders include ethylene/propylene diene terpolymer (EPDM), polytetrafluoroethylene (PTFE), polyvinylidene fluoride (PVDF), styrene/butadiene copolymer (SBR), acrylonitrile/butadiene copolymer (NBR), and carboxymethylcellulose (CMC). There is no specific limitation with respect to a method for forming the negative electrode. The negative electrode can be prepared in the same manner as in the above-mentioned method for forming the positive electrode.

There is no specific limitation with respect to the structure of the lithium secondary battery. Examples of the structures include a coin-shaped battery, a cylindrical battery, and a square-shaped battery. The coin-shaped battery comprises a positive electrode, a negative electrode, and a single-layered or a multi-layered separator. The cylindrical or square-shaped battery comprises a positive electrode, a negative electrode and a rolled separator. A known separator such as, a microporous material of polyolefin (e.g., polypropylene and polyethylene), a fabric, and a non-woven fabric can be used. The separator for the battery can be a single layered porous film or a multi-layered porous film.

The separator for the battery has a gas permeability preferably in the range of 50 to 1,000 seconds per 100 cc, more preferably in the range of 100 to 800 seconds per 100 cc, and most preferably in the range of 300 to 500 seconds per 100 cc depending on the manufacturing conditions. In the case that the gas permeability is extremely high, the conductivity of lithium ion lowers to cause unsatisfactory function as battery separator. In the case that the gas permeability is extremely low, the mechanical strength lowers. The void volume ratio preferably is in the range of 30 to 60%, more preferably in the range of 35 to 55%, and most preferably in the range of 40 to 50%. The void ratio is so adjusted as to improve the battery capacity. The thickness of the separator for the battery preferably is thin to increase the energy density. In consideration of both the mechanical strength and the performance increases, the thickness of the separator preferably is small. The thickness of the separator preferably is in the range of 5 to 50 μm, more preferably in the range of 10 to 40 μm, and most preferably in the range of 15 to 25 μm.

A favorable effect of an additive provided in the invention depends on density of an electrode material layer in a lithium secondary battery. The positive electrode composite layer formed on aluminum foil has a density of preferably in the range of 3.2 to 4.0 $g/cm^3$, more preferably in the range of 3.3 to 3.9 $g/cm^3$, and most preferably in the range of 3.4 to 3.8 $g/cm^3$. The negative electrode composite layer formed on copper foil has a density of preferably in the range of 1.3 to 2.0 $g/cm^3$, more preferably in the range of 1.4 to 1.9 $g/cm^3$, and most preferably in the range of 1.5 to 1.8 $g/cm^3$.

In the invention, the positive electrode layer can have a thickness (layer on each side of the collector) in the range of 30 to 120 μm, and more preferably in the range of 50 to 100 μm. The negative electrode layer (layer on each side of the collector) has a thickness preferably in the range of 1 to 100 µm, and more preferably in the range of 3 to 70 µm.

The lithium secondary battery of the present invention shows excellent cycle performance for a long term even in the case where the charging termination voltage is higher than 4.2 V. The battery can further show excellent cycle performance even in the case where the charging termination voltage is 4.3 V or more. The discharging termination voltage can be 2.5 V or more, and further can be 2.8 V or more. There is no specific limitation with respect to the current level. The battery is generally discharged at a constant current of 0.1 to 3 C. The lithium secondary battery of the present invention can be charged and discharged at a temperature of −40° C. or higher, and preferably at 0° C. or higher. Further, the battery can be charged and discharged at a temperature of not higher than 100° C., and preferably not higher than 80° C.

A safety valve can be attached to a sealing plate to keep the lithium secondary battery of the invention from increasing the inner pressure. A part of the battery such as, a battery cell (can) or a gasket can have a cut to avoid pressure increase. At least one of various conventional safety attachments (for example, overcurrent-preventing devices such as, a fuse, a bimetal and a FTC device) is preferably attached to the battery.

Two or more lithium secondary batteries of the invention can be placed in a battery package in series and/or parallel. A safety circuit (which has functions of monitoring conditions such as, voltage, temperature and current in each of the battery and/or in the combined batteries, and breaking the current) can be attached to the battery package in addition to a safety attachment such as, a PTC element, a thermal fuse, a fuse, and/or a current breaker.

The battery of the present invention can be used in various devices such as, a mobile phone, a notebook computer, PDA, a camcorder, a compact camera, a shaver, an electric machinery tool, and an automobile. The lithium secondary battery of the invention is highly reliable, and is advantageously used in devices requiring a charging current of 0.5 A or higher.

EXAMPLES

The present invention is described by referring to the following examples.

Example A-1

Crude tert-pentylbenzene (Comparison example X-1) was obtained by synthesis and distillation performed in the same manner as in described in J. Am. Chem. Soc., 74, 292(1952).

2.0 kg (13.5 mole) of the crude tert-pentylbenzene was placed in a flask of 3 liter volume. Nitrogen gas was bubbled into the liquid at a rate of 0.05 liter per minute while stirring. 106 g (0.66 mole) of bromine was dropwise added to the liquid at 55° C. to 60° C. for 60 minutes while irradiating with a light from a halogen lamp of 300 W. HBr gas formed at the reaction was excluded from the reaction mixture by bubbling nitrogen gas into the liquid at a rate of 0.1 liter per minute for 2 hours, and neutralized. The reaction liquid was cooled to 30° C. 71.5 g (0.37 mole) of a 28 wt. % methanol solution of sodium methoxide was dropwise added to the liquid for 30 minutes. The mixture was stirred for 30 minutes to complete neutralization. The mixture was filtered to remove precipitated NaBr. 2.15 kg of the filtered liquid was subjected to rectification using a rectification column having 10 theoretical plates at a pressure of 20 torr and at a reflux ratio of 2. Thus, 1.6 kg of pure tert-pentylbenzene was obtained as the 80% main fraction The analysis of the pure tert-pentylbenzene (Example A-1) is set forth in Table 1.

The sample was kept at 50° C. for 5 minutes, and heated to 180° C. at a rate of 10° C. per minute, and kept for 15 minutes. Impurities of the sample were then measured by means of a gas chromatography (GC-14B of Shimadzu Corporation, column: HR-1701, Detector: FID, Injection temperature: 230° C., Detector temperature: 200° C.). The amount of each of impurities was quantified in an internal standard method.

The water content was measured in the Karl Fischer method.

The sample (crude tert-pentylbenzene or purified tert-pentylbenzene) was fired in an oxygen-hydrogen flame. The formed gas was absorbed with an aqueous solution of sodium carbonate. The chlorine ion or bromine ion in the solution was measured by an ion chromatography to determine the total halogen content.

Example B-1

Crude tert-pentylbenzene (Commercially available from Tokyo Chemical Industry Co., Ltd., Comparison Example Y-1) was distilled, and further processed in the same manner as in Example A-1. The analysis of the obtained pure tert-pentylbenzene (Example B-1) is set forth in Table 1. It is apparent from comparison between Examples A-1 and B-1 that the commercially available tert-pentylbenzene is different from the tert-pentylbenzene obtained in the process of J. Am. Chem. Soc., 74, 292(1952) in impurities. It is considered that the difference in impurities is due to the difference in process for preparation of the compound.

Example B-2

A pure tert-butylbenzene was prepared in the same manner as in Example B-1, except that other crude tert-butylbenzene (Commercially available from Tokyo Chemical Industry Co., Ltd., Comparison Example Y-2) was used. The analysis of the obtained pure tert-butylbenzene (Example B-2) is set forth in Table 1.

Example B-3

A pure 1,3-di-tert-butylbenzene was prepared in the same manner as in Example B-1, except that other crude 1,3-di-tert-butylbenzene (Commercially available from Tokyo Chemical Industry Co., Ltd., Comparison Example Y-3) was used. The analysis of the obtained 1,3-di-tert-butylbenzene of high purity (Example B-3) is set forth in Table 1.

Example C-1

Preparation of Non-aqueous Electrolytic Solution

A non-aqueous solvent of EC:VC(vinylene carbonate):MEC having a volume ratio of 28:2:70 was prepared. $LiPF_6$ was dissolved in the solvent to prepare a 1 M non-aqueous electrolytic solution. 3 wt. % (based on the non-aqueous electrolytic solution) of tert-pentylbenzene of high purity prepared in Example A-1 was added to the non-aqueous electrolytic solution.

Preparation of Lithium Secondary Battery and Measurement of Battery Performance 90 wt. % of $LiCcO_2$ (positive electrode active material), 5 wt. % of acetylene black (conductive material), and 5 wt. % of polyvinylidene fluoride (binder) were mixed. 1-methyl-2-pyrrolidone was added to the mixture to give a slurry. A surface of aluminum foil was coated with the slurry. The coated foil was dried, and pressed to form a positive electrode.

95 wt. % of artificial graphite (negative electrode active material) having a graphitic crystalline structure with a distance ($d_{002}$) of 0.335 rim between lattice faces (002), and 5 wt.

% of polyvinylidene fluoride (binder) were mixed. 1-methyl-2-pyrrolidone was added to the mixture to give a slurry. A surface of copper foil was coated with the slurry. The coated foil was dried, and pressed to form a negative electrode.

A battery was prepared using a separator comprising a microporous polyethylene film (thickness: 20 μm). The non-aqueous electrolytic solution was poured into the battery. Before sealing the battery, carbon dioxide having a dew point of −60° C. was introduced into the battery to prepare a cylindrical battery having 18650 size (diameter: 18 mm, height: 65 mm). A pressure release vent and an inner current breaker (FTC element) were attached to the battery. The positive electrode had a density of 3.5 g/cm$^3$, and the negative electrode had a density of 1.6 g/Cm$^3$. The positive electrode layer had a thickness of 70 μm (layer on each side of the collector), and the negative electrode layer had a thickness of 60 μm (layer on each side of the collector).

In a cycle test, the 18650 battery was charged with a constant current of 2.2 A (1C) at an elevated temperature (45° C.) to reach 4.3 V. The battery was further charged under the constant voltage for 3 hours in total to reach the terminal charging voltage of 4.3 V. The battery was discharged under the constant current of 2.2 A (1C) to reach the charging voltage of 3.0 V. The charge and the discharge were repeated. The initial discharging capacity (mAh) was equivalent to the result of the case (Comparison example Z-1) that 3 wt. % of crude tert-pentylbenzene was added to the non-aqueous electrolytic solution in place of the purified tert-pentylbenzene of Example A-1 to prepare an electrolytic solution of 1 M LiPF$_6$+EC/VC/MEC having a volume ratio of 28/2/70. The battery performance was measured after 100 cycles, and the retention of the discharging capacity relative to the initial discharging capacity (100%) was 92.1%. Further, the amount of the generated gas after 100 cycles was remarkably smaller than that in the case of using the Comparative example X-1. The conditions in preparation and the battery performance of 18650 battery are set forth in Table 2.

Examples C-2 to C-4

Cylindrical batteries were prepared in the same manner as in Example C-1, except that 3 wt. % of the tert-alkylbenzene compounds of the Examples B-1 to B-3 were respectively added to the non-aqueous electrolytic solutions. The conditions of the materials in preparation and the retention of the discharging capacity after 100 cycles of the cylindrical battery of 18650 size are set forth in Table 2.

Example C-5

A cylindrical battery was prepared in the same manner as in Example C-1, except that 1 wt. % of the pure tert-alkylbenzene compound of the Example A-1 was added to the non-aqueous electrolytic solution. The conditions of the materials in preparation and the retention of the discharging capacity after 100 cycles of the cylindrical battery of 18650 size are set forth in Table 2.

Example C-6

A non-aqueous solvent of EC:VC:MEC having a volume ratio of 28:2:70 was prepared. 0.95 M of LiPF$_6$ and 0.05 M of LiBF$_4$ were dissolved in the solvent to prepare a non-aqueous electrolytic solution. 3 wt. % (based on the non-aqueous electrolytic solution) of the tert-pentylbenzene of high purity of Example A-1 was added to the non-aqueous electrolytic solution. A cylindrical battery was prepared in the same manner as in Example C-1, except that the above-prepared non-aqueous electrolytic solution was used. The conditions of the materials in preparation and the retention of the discharging capacity after 100 cycles of the cylindrical battery of 18650 size are set forth in Table 2.

Examples D-1 and D-2

Cylindrical batteries were prepared in the same manner as in Example C-1, except that LiCo$_{1/3}$Ni$_{1/3}$Mn$_{1/3}$O$_2$ was used as the positive active substance in place of LiCoO$_2$, and 3 wt. % (based on the non-aqueous electrolytic solution) of the pure tert-alkylbenzene compounds of Examples A-1 and B-2 were respectively used. The conditions of the materials in preparation and the retention of the discharging capacity after 100 cycles of the cylindrical battery of 18650 size are set forth in Table 2.

Comparison Example Z-1

A cylindrical battery was prepared in the same manner as in Example 1, except that 3 wt. % of the crude tert-alkylbenzene compound of the Comparison example X-1 was added to the non-aqueous electrolytic solution. The conditions of the materials in preparation and the retention of the discharging capacity after 100 cycles of the cylindrical battery of 18650 size are set forth in Table 2.

Comparison Examples Z-2 to Z-4

Cylindrical batteries were prepared in the same manner as in Example 1, except that 3 wt. % of the crude tert-alkylbenzene compounds of the Comparison examples Y-1 to Y-3 were respectively added to the non-aqueous electrolytic solution. The conditions of the materials in preparation and the retention of the discharging capacity after 100 cycles of the cylindrical battery of 18650 size are set forth in Table 2.

TABLE 1

| | Example | | | |
| --- | --- | --- | --- | --- |
| | A-1 | B-1 | B-2 | B-3 |
| Tert-alkylbenzene compound | Tert-pentylbenzene (synthesized sample 1) | Tert-pentyl-benzene (product of Tokyo Chemical Industry) | Tert-butyl-benzene (product of Tokyo Chemical Industry) | 1,3-Di-tert-pentyl-benzene (synthesized sample 4) |

TABLE 1-continued

| | | | | |
|---|---|---|---|---|
| Alkylbenzene compound having a benzene ring via tertiary carbon atom (%) | 1,2-Dimethyl-propylbenzene (0.05) Dimethylindan (<0.01) Isopropylbenzene (<0.01) 1-Methyl-tetra-hydronaphthalene (<0.01) | Isopropylbenzne (0.05) Dimethylindan (<0.01) | Sec-butyl-benzene (0.05) Isopropylbenzene (<0.01) | 1-Tert-butyl-3-isopropylbenzene (0.08) |
| Purity (%) | >99.9 | >99.9 | >99.9 | 99.7 |
| Water content (ppm) | 20 | 20 | 20 | 20 |
| Halogen (ppm) | <40 | <30 | <40 | <40 |

| | Comparison example | | | |
|---|---|---|---|---|
| | X-1 | Y-1 | Y-2 | Y-3 |
| Tert-alkylbenzene compound | Tert-pentylbenzene (synthesized sample 1) | Tert-pentyl-benzene (product of Tokyo Chemical Industry) | Tert-butyl-benzene (product of Tokyo Chemical Industry) | 1,3-Di-tert-pentyl-benzene (synthesized sample 4) |
| Alkylbenzene compound having a benzene ring via tertiary carbon atom (%) | 1,2-Dimethyl-propylbenzene (3.1) Dimethylindan (0.4) Isopropylbenzene (0.2) 1-Methyltetra-hydronaphthalene (0.1) | Isopropylbenzne (1.3) Dimethylindan (0.4) | Sec-butyl-benzene (0.8) Isopropylbenzene (0.2) | 1-Tert-butyl-3-isopropylbenzene (1.6) |
| Purity (%) | 95.9 | 98.1 | 98.6 | 97.8 |
| Water content (ppm) | 150 | 120 | 150 | 150 |
| Halogen (ppm) | <40 | <10 | <40 | <40 |

TABLE 2

| | Tert-alkyl-benzene compound | Added amount (wt. %) | Composition of non-aqueous electrolytic solution (Volume ratio) | Retention of discharging capacity (%) after 100 cycles |
|---|---|---|---|---|
| Example | | | | |
| C-1 | A-1 | 3 | 1M LiPF6 EC/VC/MEC = 28/2/70 | 92.1 |
| C-2 | B-1 | 3 | 1M LiPF6 EC/VC/MEC = 28/2/70 | 91.7 |
| C-3 | B-2 | 3 | 1M LiPF6 EC/VC/MEC = 28/2/70 | 91.1 |
| C-4 | B-3 | 3 | 1M LiPF6 EC/VC/MEC = 28/2/70 | 90.7 |
| C-5 | A-1 | 1 | 1M LiPF6 EC/VC/MEC = 28/2/70 | 91.4 |
| C-6 | A-1 | 3 | 0.95M LiPF6 + 0.05M LiBF4 EC/VC/MEC = 28/2/70 | 92.5 |
| Comparison example | | | | |
| Z-1 | X-1 | 3 | 1M LiPF6 EC/VC/MEC = 28/2/70 | 87.2 |
| Z-2 | Y-1 | 3 | 1M LiPF6 EC/VC/MEC = 28/2/70 | 87.4 |
| Z-3 | Y-2 | 3 | 1M LiPF6 EC/VC/MEC = 28/2/70 | 85.2 |
| Z-4 | Y-3 | 3 | 1M LiPF6 EC/VC/MEC = 28/2/70 | 86.4 |

TABLE 3

| Example | Positive electrode | Tert-alkyl-benzene compound | Added amount (wt. %) | Composition of non-aqueous electrolytic solution (Volume ratio) | Retention of discharging capacity (%) after 100 cycles |
|---|---|---|---|---|---|
| D-1 | LiCo$_{1/3}$Ni$_{1/3}$Mn$_{1/3}$O$_2$ | A-1 | 3 | 1M LiPF6 EC/VC/MEC = 28/2/70 | 91.6 |
| D-2 | LiCo$_{1/3}$Ni$_{1/3}$Mn$_{1/3}$O$_2$ | B-2 | 3 | 1M LiPF6 EC/VC/MEC = 28/2/70 | 91.5 |

The invention claimed is:

1. A non-aqueous electrolytic solution for a lithium secondary battery which comprises an electrolyte salt in a non-aqueous solvent, which contains a tert-alkylbenzene compound in an amount of 0.1 to 10 wt. % based on an amount of the solution and which further contains a benzene compound having a benzene ring substituted with a hydrocarbon group having 1 to 4 carbon atoms via at least one tertiary carbon atom, in an amount of 0.5 wt. % or less and more than 0.001 wt. % based on the amount of the tert-alkylbenzene compound,
    wherein the tert-alkylbenzene compound is at least one of tert-butylbenzene, tert-pentylbenzene, 1,4-di-tert-butylbenzene, 4-fluoro-tert-butylbenzene, 4-tert-butylbiphenyl, 1,3-di-tert-pentylbenzene, 1,4-di-tert-pentylbenzene, or 1-tert-butyl-4-tert-pentylbenzene, and
    wherein the benzene compound having a benzene ring substituted with a hydrocarbon group having 1 to 4 carbon atoms via at least one tertiary carbon atom is at least one of sec-butylbenzene, isopropylbenzene, 1,2-dimethylpropylbenzene, 1,2-dimethylindan, 1,3-dimethylindan, 1-methyltetrahydronaphthalene, 1-tert-butyl-3-isopropylbenzene, 1-tert-butyl-4-isopropylbenzene, 4-fluoro-isopropylbenzene, 4-fluoro-sec-butylbenzene, 4-sec-butylbiphenyl, 1-tert-pentyl-3-isoprolpylbenzene, or 1-tert-pentpyl-4-isopropylbenzene.

2. The non-aqueous electrolytic solution of claim 1, wherein the tert-alkylbenzene compound is tert-butylbenzene, and the benzene compound having the benzene ring substituted with the hydrocarbon group having 1 to 4 carbon atoms via at least one tertiary carbon atom comprises sec-butylbenzene and/or isopropylbenzene.

3. The non-aqueous electrolytic solution of claim 1, wherein the tert-alkylbenzene compound is tert-pentylbenzene, and the benzene compound having the benzene ring substituted with the hydrocarbon group having 1 to 4 carbon atoms via at least one tertiary carbon atom comprises isopropylbenzene, 1,2-dimethylpropylbenzene, 1,2-dimethylindan, 1,3-dimethylindan, and/or 1-methyltetrahydronaphthalene.

4. The non-aqueous electrolytic solution of claim 1, wherein the tert-alkylbenzene compound is 1,3-di-tert-butylbenzene, and the benzene compound having the benzene ring substituted with the hydrocarbon group having 1 to 4 carbon atoms via at least one tertiary carbon atom is 1-tert-butyl-3-isopropylbenzene.

5. The non-aqueous electrolytic solution of claim 1, wherein the tert-alkylbenzene compound is 1,4-di-tert-butylbenzene, and the benzene compound having the benzene ring substituted with the hydrocarbon group having 1 to 4 carbon atoms via at least one tertiary carbon atom is 1-tert-butyl-4-isopropylbenzene.

6. The non-aqueous electrolytic solution of claim 1, wherein the tert-alkylbenzene compound is 4-fluoro-tert-butylbenzene, and the benzene compound having the benzene ring substituted with the hydrocarbon group having 1 to 4 carbon atoms via at least one tertiary carbon atom comprises 4-fluoro-isopropylbenzene and/or 4-fluoro-sec-butylbenzene.

7. The non-aqueous electrolytic solution of claim 1, wherein the tert-alkylbenzene compound is 4-tert-butylbiphenyl, and the benzene compound having the benzene ring substituted with the hydrocarbon group having 1 to 4 carbon atoms via at least one tertiary carbon atom is 4-sec-butylbiphenyl.

8. The non-aqueous electrolytic solution of claim 1, wherein the tert-alkylbenzene compound is 1,3-di-tert-pentylbenzene, and the benzene compound having the benzene ring substituted with the hydrocarbon group having 1 to 4 carbon atoms via at least one tertiary carbon atom is 1-tert-pentyl-3-isopropylbenzene.

9. The non-aqueous electrolytic solution of claim 1, wherein the tert-alkylbenzene compound is 1,4-di-tert-pentylbenzene, and the benzene compound having the benzene ring substituted with the hydrocarbon group having 1 to 4 carbon atoms via at least one tertiary carbon atom is 1-tert-pentyl-4-isopropylbenzene.

10. The non-aqueous electrolytic solution of claim 1, wherein the tert-alkylbenzene compound is 1-tert-butyl-4-tert-pentylbenzene, and the benzene compound having the benzene ring substituted with the hydrocarbon group having 1 to 4 carbon atoms via at least one tertiary carbon atom is 1-tert-butyl-4-isopropylbenzene.

11. A lithium secondary battery comprising a positive electrode, a negative electrode and a non-aqueous electrolytic solution comprising an electrolyte salt in a non-aqueous solvent, wherein the non-aqueous electrolytic solution is the non-aqueous electrolytic solution defined in claim 1.

* * * * *